United States Patent
Sobral et al.

(10) Patent No.: US 9,090,607 B2
(45) Date of Patent: Jul. 28, 2015

(54) PROCESS FOR PREPARING TIOTROPIUM BROMIDE

(71) Applicant: Hovione International Limited, Wanchai (CN)

(72) Inventors: Luis Sobral, Loures (PT); Marcio Temtem, Quinta do Conde (PT); Rafael Antunes, Setúbal (PT); Bruna Nunes, Alverca (PT)

(73) Assignee: Hovione International Limited, Wanchai (CN)

( * ) Notice: Subject to any disclaimer, the term of this patent is extended or adjusted under 35 U.S.C. 154(b) by 0 days.

(21) Appl. No.: 14/377,271

(22) PCT Filed: Feb. 8, 2013

(86) PCT No.: PCT/GB2013/000050
§ 371 (c)(1),
(2) Date: Aug. 7, 2014

(87) PCT Pub. No.: WO2013/117886
PCT Pub. Date: Aug. 15, 2013

(65) Prior Publication Data
US 2015/0018556 A1    Jan. 15, 2015

(30) Foreign Application Priority Data
Feb. 10, 2012 (PT) .......................................... 106142

(51) Int. Cl.
C07D 491/08    (2006.01)
C07D 451/14    (2006.01)
C07D 451/10    (2006.01)

(52) U.S. Cl.
CPC ............ C07D 451/14 (2013.01); C07D 451/10 (2013.01)

(58) Field of Classification Search
CPC ....................................................... C07D 451/10
USPC ............................................................. 546/91
See application file for complete search history.

(56) References Cited

U.S. PATENT DOCUMENTS

| | | |
|---|---|---|
| 6,486,321 B2 | 11/2002 | Banholzer et al. |
| 6,747,154 B2 | 6/2004 | Brandenburg et al. |
| 6,777,423 B2 | 8/2004 | Banholzer et al. |
| 7,662,963 B2 | 2/2010 | Busolli et al. |
| 2008/0051582 A1 | 2/2008 | Busolli et al. |
| 2010/0215590 A1 | 8/2010 | Rasenack et al. |

FOREIGN PATENT DOCUMENTS

| | | |
|---|---|---|
| EP | 0418716 A1 | 3/1991 |
| EP | 1410144 A1 | 4/2004 |
| EP | 1682544 A2 | 7/2006 |
| EP | 1869035 A2 | 12/2007 |
| EP | 1879888 A2 | 1/2008 |
| EP | 2085396 A2 | 8/2009 |
| WO | 2007022531 A2 | 2/2007 |
| WO | 2007075858 A2 | 7/2007 |
| WO | 2009087419 A1 | 7/2009 |
| WO | 2011015882 A2 | 2/2011 |
| WO | 2011015884 A1 | 2/2011 |

OTHER PUBLICATIONS

PCT International Search Report, Application No. PCT/GB2013/000050, dated Apr. 3, 2013.

*Primary Examiner* — Nizal Chandrakumar
(74) *Attorney, Agent, or Firm* — MacMillan, Sobanski & Todd, LLC (57) ABSTRACT

The present invention relates to a novel process for the preparation of tiotropium bromide there is provided a process for preparing tiotropium bromide comprising (i) reacting scopine oxalate with diethylamine in an inert solvent to form scopine; (ii) reacting scopine and methyl di-(2-dithienyl)glycolate (MDTG) in the presence of an inorganic base, and in an inert solvent to form N-demethyltiotropium; (iii) reacting N-demethyltiotropium with bromomethane in an inert solvent to form tiotropium bromide; (iv) crystallizing tiotropium bromide in a mixture of methanol and acetone, and optionally thereafter, (v) micronizing the tiotropium bromide so formed.

31 Claims, 11 Drawing Sheets

Figure 1: XRPD diffractogram of tiotropium bromide crystallized from methanol/acetone Figure 2: DSC thermogram of tiotropium bromide crystallized from methanol/acetone Figure 3: TGA thermogram of tiotropium bromide crystallized from methanol/acetone Figure 4: XRPD of Tiotropium Bromide methanol solvate Figure 5: XRPD of Tiotropium Bromide after drying under vacuum at 90 °C for 9 hours Figure 6: XRPD of Tiotropium Bromide obtained by methanol/acetone (1:1) recrystallization Figure 7: XRPD of Tiotropium Bromide obtained by methanol/acetone (1:3) recrystallization Figure 8: XRPD of Tiotropium Bromide obtained by methanol/acetone (1:6) recrystallization Figure 9: XRPD of Tiotropium Bromide obtained by methanol/acetone (3:1) recrystallization Figure 10: XRPD of Tiotropium Bromide obtained by methanol/acetone (6:1) recrystallization Figure 11: XRPD of Tiotropium Bromide before and after micronisation

PROCESS FOR PREPARING TIOTROPIUM BROMIDE

This is a national stage application filed under 35 U.S.C. §371 of international application PCT/GB2013/000050, filed on Feb. 8, 2013, published; which claims the benefit of Portugese Patent Application 106142, filed on Feb. 10, 2012. The entire disclosures of all the aforementioned applications are incorporated herein by reference for all purposes.

This invention relates to a new process for preparing (1α,2β,4β,5α,7β)-7-[(hydroxydi-2-thienylacetyl)oxy]-9,9-dimethyl-3-oxa-9-azoniatricyclo[3.3.1.0$^{2,4}$]nonane bromide, a compound known by the name tiotropium bromide, which process comprises the following steps: a) reaction of (1α,2β,4β,5α,7β)-9-methyl-3-oxa-9-azatricyclo[3.3.1.0$^{2,4}$]nonan-7-ol oxalate (also known as scopine oxalate) with diethylamine to prepare (1α,2β,4β,5α,7β)-9-methyl-3-oxa-9-azatricyclo[3.3.1.0$^{2,4}$]nonan-7-ol (also known as scopine) b) reaction of scopine with methyl di-(2-dithienyl)glycolate (also known as MDTG) and potassium carbonate to prepare 9-methyl-3-oxa-9-azatricyclo[3.3.1.0$^{2,4}$]non-7-yl hydroxy(dithiophen-2-yl)acetate (also known as N-demethyltiotropium or scopine di-(2-thienyl)glycolate) with consistent high purity c) reaction of N-demethyltiotropium with bromomethane to prepare tiotropium bromide d) crystallization of crude tiotropium bromide to consistently obtain product with high polymorphic purity and optionally e) micronizing tiotropium bromide to obtain product with adequate particle size for inhalation while maintaining its polymorphic form.

This invention relates to a new process for the preparation of tiotropium bromide which is an effective anthicolinergic agent and has been used in the treatment of respiratory diseases such as asthma or chronic obstructive pulmonary disease (COPD).

BACKGROUND OF THE INVENTION

The compound tiotropium bromide (1) whose molecular structure is depicted below is known from the European Patent Application EP0418716.

(I)

Tiotropium bromide is a highly effective active pharmaceutical ingredient which is administrated in low (microgram) therapeutic doses by inhalation. Highly effective pharmaceutical, active substances used for preparing pharmaceutical compositions suitable for administration by inhalation have to be of high chemical purity and have to be of high polymorphic purity. Crystalline polymorphic forms of tiotropium bromide have been reported in various publications (U.S. Pat. No. 6,777,423; EP14101445; EP16825442; EP1879888; EP2085396; EP1869035; and WO2011/015882) showing that the compound may give rise to a variety of solids having distinct physical properties. This invention discloses a process for the preparation of tiotropium bromide which consistently affords product with outstanding chemical purity and which affords a single, pure polymorph with a consistent level of polymorphic purity.

The preparation of tiotropium bromide was first disclosed in EP0418716 and the synthesis described in this patent involves the transesterification reaction between scopine (ii) and MDTG (III), to prepare N-demethyltiotropium (IV), followed by reaction of N-demethyltiotropium with bromomethane to prepare tiotropium bromide (Scheme 1).

Scheme 1: Tiotropium bromide synthetic route disclosed in EP418716

One disadvantage of this route is the use of scopine as a starting material because scopine is a sensitive compound that tends to liquefy when exposed to air and, due to its inherent instability, it is not commercially available. Another disadvantage is the use of hazardous reagents, such as sodium metal, in the transesterification reaction to form N-demethyltiotropium. The yields reported for the preparation of N-demethyltiotropium vary between 45% and 70% (of theoretical) but the highest yield is obtained when the transesterification reaction is carried out in a melted mixture of scopine and MDTG, what is a cumbersome procedure to employ in an industrial process.

U.S. Pat. No. 6,486,321 describes an alternative process for the preparation of tiotropium bromide which starts from tropenol (V) hydrochloride. However, this process is more complex than the process disclosed in EP0418716 because it encompasses a longer synthetic route than that of EP0418716 (Scheme 2).

Scheme 2: Tiotropium bromide synthetic route disclosed in U.S. Pat. No. 6,486,321

(V)
(III)
(VI)
(IV)
(I)

U.S. Pat. No. 6,747,154 describes a short route of synthesis to prepare tiotropium bromide where this product is prepared by a direct coupling reaction between MTDG and scopine methyl bromide (VII) in the presence of a coupling agent such as carbonildiimidazolide and of bases such as alkali metal imidozolides (Scheme 3). However, details on the purity of the products obtained according to the process claimed are not disclosed. In addition to the absence of details on the purity, the product obtained by following the claimed process is purified and the yield reported for the purification is low, 74% (w/w). In spite of following a short synthetic route, the process requires the use of hazardous reagents such as alkali metals or alkali hydride metals (such as lithium hydride) to prepare the metal salts of the bases. Another disadvantage of this process is that the coupling agents employed (carbonyldiimidazole, or carbonyldi-1,2,4-triazole or dicyclohexylcarbodiimide) are expensive reagents.

Scheme 3: Tiotropium bromide synthetic route disclosed in U.S. Pat. No. 6,747,154

(VII)
(III)
(I)

U.S. Pat. No. 7,662,963 describes the preparation of N-demethyltiotropium by reaction of a scopine salt of formula (IX) with MDTG, in the presence of a weak inorganic base, and in a polar organic solvent (Scheme 4). The salts of scopine disclosed are the bromide (X is Br⁻), the chloride (X is Cl⁻), the sulfate (X is $SO_4^{2-}$), the acetate (X is $CH_3COO^-$), the phosphate (X is $PO_4^{2-}$), the methane sulfonate (X is $CH_3SO_3^-$), the tartarate, the fumarate, the citrate, the maleate, the succinate, the p-toluene sulphonate and the amido sulphonate. However, the purities (by HPLC) reported in examples for the preparation of N-demethyltiotropium process are of 70% (example 12), 98.3% (examples 11 and 21) and 98.5% (example 13). In comparison, the purity of N-demethyltiotropium obtained according to the process of the present invention is greater than 99.0%.

Scheme 4: Synthesis of N-demethyltiotropium claimed in U.S. Pat. No. 7,662,963

(IX)

Weak inorganic base
Polar organic solvent

WO2009087419 describes a process to prepare N-demethyltiotropium (which is designated as tiotropium base) and tiotropium bromide with a purity greater than 95%, by HPLC, said process comprising the transesterification of scopine, or a salt thereof such as scopine hydrochloride, with MDTG in the presence of an organic amine base such as 1,8-diazabicyclo[5.4.0]undec-7-ene (DBU) and a further base such as an inorganic base. An inorganic base such as sodium hydride (NaH) is used to liberate scopine from the corresponding hydrochloride salt. Although the application states that the use of DBU is very advantageous because it allows N-demethyltiotropim to be prepared with a purity of preferably greater than 99% by HPLC, no details are disclosed in the description of the process explaining how such a high purity can be achieved. In addition, the sole example reporting the purity of N-demethyltiotropium presents a purity of 98% by HPLC. To obtain N-demethyltiotropium with purity higher than 98% the material obtained according to the claimed process is recrystallized from acetonitrile and the yield reported is only 86% (w/w); the purity reported for the crystallized product is 99.8% by HPLC. In the example describing an alternative process to prepare tiotropium bromide, which is a telescoped process where the intermediate N-demethyltiotropium bromide is not isolated and is used in solution for the reaction with methyl bromide, the purity reported for the tiotropium bromide obtained is 98.66%. The examples presented also show that, tiotropium bromide 99.83% pure by HPLC is obtained from crystallized N-demethyltiotropium (material with a purity greater than 99.8% by HPLC) whilst tiotropium bromide with a purity of only 98.66% by HPLC is obtained from N-demethyltiotropium that is not crystallized.

WO2011/015884 describes a process to prepare N-demethyltiotropium and tiotropium bromide in substantially pure form, which process comprises the transesterificaiion of scopine, or a salt thereof, with MDTG, wherein the transesterification reaction is performed in the presence of an organic base such as DBU and an inorganic base such as potassium carbonate. The application states that N-demethyltiotropium and the tiotropium bromide obtained by the process claimed have a purity of at least 99% by HPLC. The example presented for the preparation of N-demethyltiotropium refers to a product with a purity of 98.7% and the example for the preparation of tiotropium bromide refers to a product with a purity of 99.9%. One disadvantage of this process is that two bases are required to obtain N-demethyltiotropium with purity of 99% by HPLC. The other disadvantage is that the organic bases claimed (triethylamine, diisopropylethylamine, DBU, DBN, DMAP) are very expensive when compared to potassium carbonate and, the amount of organic base used is significant (3 eq.). Surprisingly, the present invention shows that N-demethyltiotropium cap be prepared with purity greater than, 99.0%, by HPLC using only potassium carbonate, a cheap base which can be easily eliminated from the process as shown below. It also shows that tiotropium bromide with purity equal to, or greater than, 99.5% by HPLC can be prepared by following the process of the present invention.

According to a first aspect of the present invention, there is provided a process for preparing N-demethyltiotropium with purity greater than 99.0% by HPLC. In this process, scopine oxalate is, treated with diethylamine to afford scopine, and the scopine so formed is combined with MDTG in the presence of anhydrous potassium carbonate to form N-demethyltiotropium. Surprisingly, it has been found that N-demethyltiotropium can be obtained in very high purity when prepared according to the process of the present invention. Since the purity of this compound is very high, it can be used in the synthesis of tiotropium bromide without further purification and allows tiotropium bromide with purity greater than 99.5% to be prepared. By avoiding a purification step this approach a great benefit in a commercial process as it saves significant amounts of time and costs. In a second aspect, the present invention provides a process for manufacturing tiotropium bromide with a high purity, equal to, or greater than 99.5%.

WO2007/0225314 describes three different crystalline forms of tiotropium bromide which may be prepared by crystallizing the product from methanol and acetone. According to the application, Form 1 can be obtained by crystallizing the product from a mixture of methanol and acetone with a ratio of 1/1 (vol./vol.), Form 2 can be obtained by crystallization from a mixture of methanol and acetone with a ratio ranging from 1/1 (vol./vol.) to ⅓, and Form 3 can be obtained by crystallization from a mixture of methanol and acetone with a ratio of 3/1 (vol./vol.).

Surprisingly, it has been found that the process of this invention affords tiotropium bromide in a single and pure crystalline form. The process of the present invention encompasses a crystallization of tiotropium bromide from mixtures of methanol and acetone with different proportions, wherein a single crystalline form is obtained regardless of the proportion of methanol and acetone employed in the crystallization. When carrying out the crystallization of tiotropium bromide in mixtures of methanol and acetone with a methanol proportion higher than acetone e.g. methanol and acetone 3/1 (vol./vol.), or a proportion of acetone higher than methanol e.g. pethanol and acetone ⅓ (vol./vol.) or even with the same proportion of methanol and acetone, the process of this invention consistently affords a single and pure anhydrous crystalline form. Hence, in a third aspect, the present invention provides a process to consistently obtain a single pure anhydrous crystalline form of tiotropium bromide.

Finally, a fourth aspect of the present invention is the development of a suitable micronization method to obtain tiotropium bromide with adequate particle size for inhalation while maintaining its polymorphic form.

Jet milling is the most often employed process for the micronization of inhalation products. US2010/0215590 describes a process for the production of virtually anhydrous micronized tiotropium bromide comprising the use of monohydrate tiotropium monohydrate as raw material. The process described is conducted using a gas jet mill which is known as a high energy size reduction process that breaks down active substance crystals, impacting surface energy and crystal form. The output material often contains significant amounts of amorphous material, which can influence both the stability of the finished product and the formulation. Surprisingly, the current invention uses a milling process that maintains the polymorphic form of tiotroprium bromide and allows controlling the particle size.

DETAILED DESCRIPTION OF THE INVENTION

According to a first embodiment of the present invention, there is provided a process for preparing tiotropium bromide comprising:
  i) reacting scopine oxalate with diethylamine in an inert solvent to form scopine;
  ii) reacting scopine and methyl di-(2-dithienyl)glycolate (MDTG) in the presence of an inorganic base, and in an inert solvent to form N-demethyltiotropium;
  iii) reacting N-demethyltiotropium with bromomethane in an inert solvent to form tiotropium bromide;
  iv) crystallizing bromide, in a mixture of methanol and acetone, and optionally thereafter,
  v) micronizing the tiotropium bromide so formed.

The process for the manufacture of tiotropium bromide preferably comprises the following steps:
  i) reacting scopine oxalate (X) with diethylamine in an inert solvent, preferably at a temperature between about 30° C. to about 45° C., to form scopine (II), and preferably thereafter removing any diethylammonium oxalate salt so formed from the reaction mixture, preferably by filtration, and performing a solvent exchange;
  ii) reacting scopine and MDTG in the presence of a suitable inorganic base such as potassium carbonate in an inert solvent, preferably at a temperature between about 80° C. and about 110° C., to form N-demethyltiotropium, and preferably thereafter removing any inorganic salts present in the reaction mixture, preferably by filtration;
  iii) preferably treating the reaction mixture containing N-demethyltiotropium with water or brine (to remove the major by-product of the transesterification reaction 2-hydroxy-2,2-di(thiophene-2-yl)acetic) (X), herein designated as DTG), concentrating the resulting solution to crystallize the N-demethyltiotropium present from solution; and thereafter isolating, preferably by filtration and drying, N-demethyltiotropium with a purity greater than 99.0% by HPLC;
  iv) reacting N-demethyltiotropium with bromomethane in an inert solvent, preferably at a temperature between about 0° C. and about 25° C., to form tiotropium bromide (wherein at least part of the desired product precipitates from the reaction mixture), and preferably thereafter adding a suitable anti-solvent (to effect further precipitation) optionally, further slurrying the tiotropium bromide so formed in a mixture of a suitable inert solvent and a suitable anti-solvent, and isolating the product so formed, preferably by filtration and drying, with a purity equal to, or greater than, 99.5% by HPLC,
  v) crystallizing the tiotropium bromide in a mixture of methanol and acetone, to obtain product with a purity greater than 99.5% by HPLC and in a single anhydrous crystalline form; and optionally thereafter micronizing the tiotropium bromide so formed.

In a preferred embodiment, the solvent of step i) for the reaction of diethylamine with scopine oxalate is selected from the group consisting of halogenated hydrocarbons such as dichloromethane and ketones such as acetone. Preferably, the solvent is acetone. In a more preferred embodiment, the reaction is carried out at temperature between about 40° C. and about 45° C. because temperatures higher than about 45° C. promote the isomerization of scopine into scopoline (XI).

In another preferred embodiment, the solvent of step ii) for the transesterification reaction is selected from the group consisting of mixtures of hydrocarbons such as n-heptane and amides such as dimethylformamide. Preferably, the solvent is a mixture of n-heptane with dimethylformamide, more preferably in a proportion of 10 vols. of n-heptane and 1 vol. of dimethylformamide.

In another preferred embodiment, the inorganic base of step ii) is selected from the group consisting of anhydrous potassium carbonate, anhydrous cesium carbonate and potassium tert-butoxide. Preferably, the inorganic base is anhydrous potassium carbonate.

In another preferred embodiment, the transesterification reaction is carried out at temperature between 85° C. and 100° C., more preferably at temperatures between about 90° C. and about 95° C. At temperatures higher than about 110° C. significant amounts of the by product DTG form and at temperatures lower than about 85° C. the reaction is slow.

Upon completion of the reaction of step ii), the inorganic salts are removed by filtration and the filtered organic solution (containing N-demethyltiotropium) is washed with brine, or with water, to remove the major by-product of the transesterification reaction, DTG. The organic solution obtained after the water (or brine) washes contains at least 90% of N-demethyltiotropium by HPLC. In another embodiment, the present invention provides a process for purification of the transesterification reaction mixture which comprises purging the by-product DTG with water or brine to afford a solution containing at least 90% by HPLC of N-demethyltiotropium. The organic solution obtained after the water (or brine) washes is treated with activated charcoal to remove color and afterwards is concentrated under reduced pressure to crystallize the product.

In another preferred embodiment, the methylation reaction of step iv) can be carried out in a solvent selected from the group consisting of imides such as dimethylformamide, cyclic ethers such as tetrahydrofuran or 2-methyltetrahydrofuran, nitriles such as acetonitrile, mixtures of acetone with tetrahydrofuran and of ethyl acetate with tetrahydrofuran. Preferably, the solvent is dimethylformamide. In a more preferred embodiment, the methylation reaction is carried out at a first temperature of between about 0° C. and about 5° C. (preferably for a time period of between about 8 to about 15 hours), followed by a second temperature of between about 10° C. and about 15° C. (preferably for a time period of up to about 5 hours for example, 1, 2, 3, 4, or 5 hours), followed by a third temperature between about 20 and about 25° C. (preferably for a time period of up to about 5 hours, for example, 1, 2, 3, 4, or 5 hours). By following this temperature gradient it is possible to consume the starting material N-demethyltiotropium down to levels equal to, or lower than 1.0% and consequently to obtain tiotropium bromide with a residual content of N-demethyltiotropium below 0.2%. Part of the product precipitates during the methylation reaction and when the reaction is complete, 2-methyltetrahydrofuran is added to the reaction mixture as an anti-solvent to precipitate more product. The addition of an anti-solvent allows crude tiotropium bromide to be obtained in yields up to 91% (% of the theoretical). The purity of the product obtained by following the procedure described above is equal to, or greater than, 99.4% by HPLC. Therefore, in another embodiment, the present invention provides a process for preparing crude tiotropium bromide with purity equal to, or greater than, 99.4% by HPLC.

Figure 1:
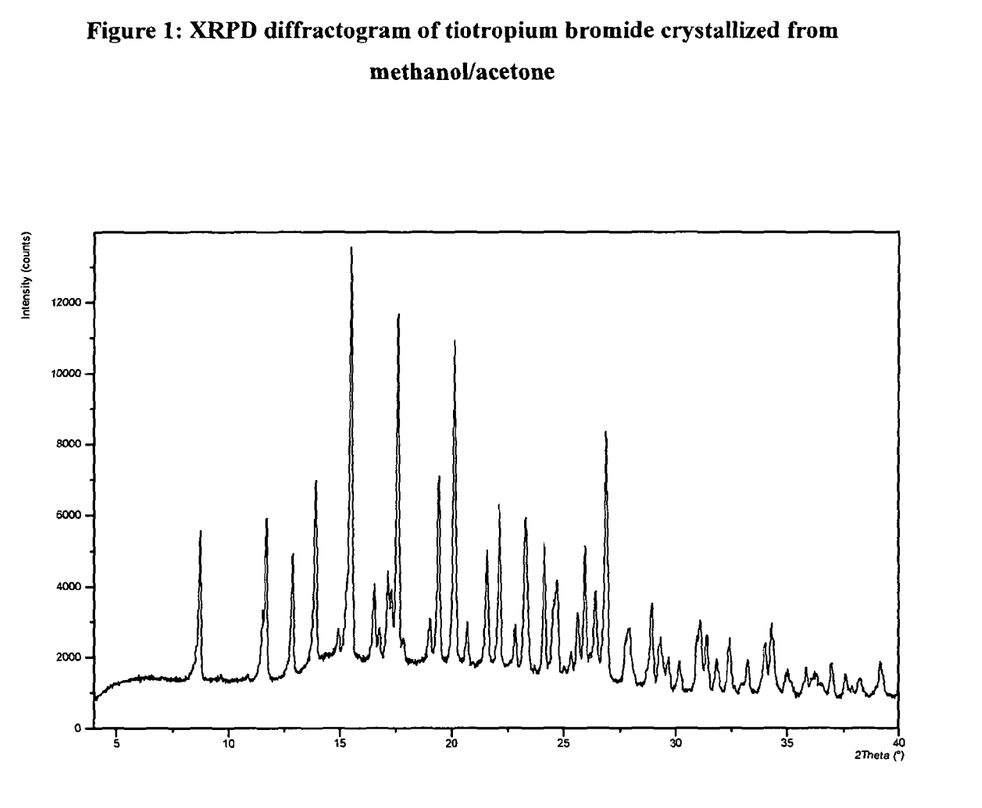
FIG. 1: XRPD diffractogram of tiotropium bromide crystallized from methanol/acetone.
Figure 2:
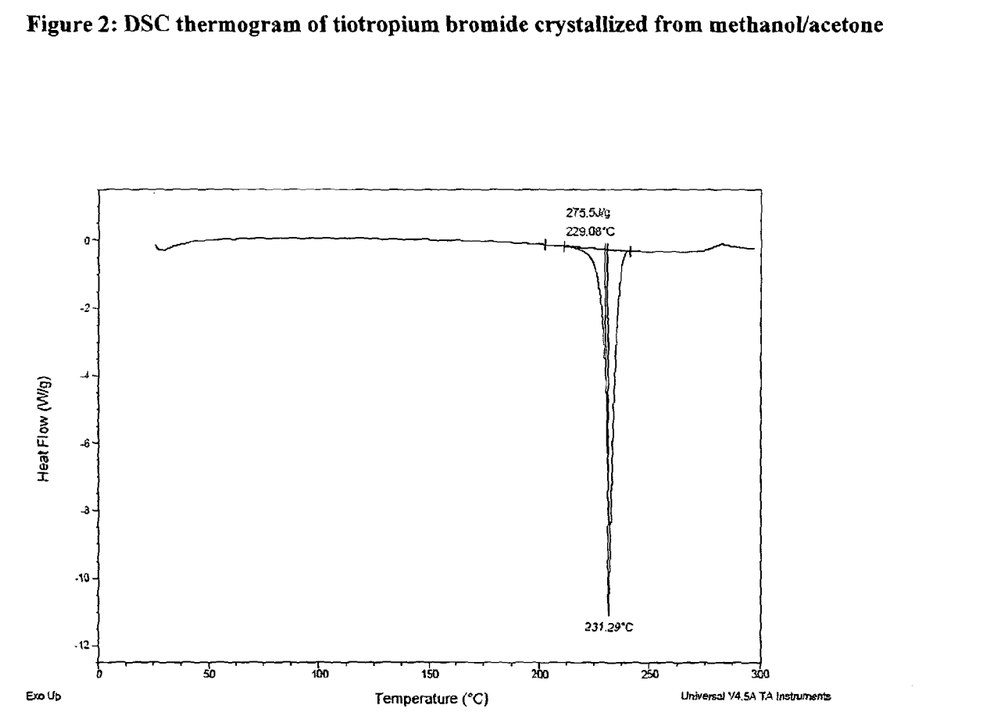
FIG. 2: DSC thermogram of tiotropium bromide crystallized from methanol/acetone.
Figure 3:
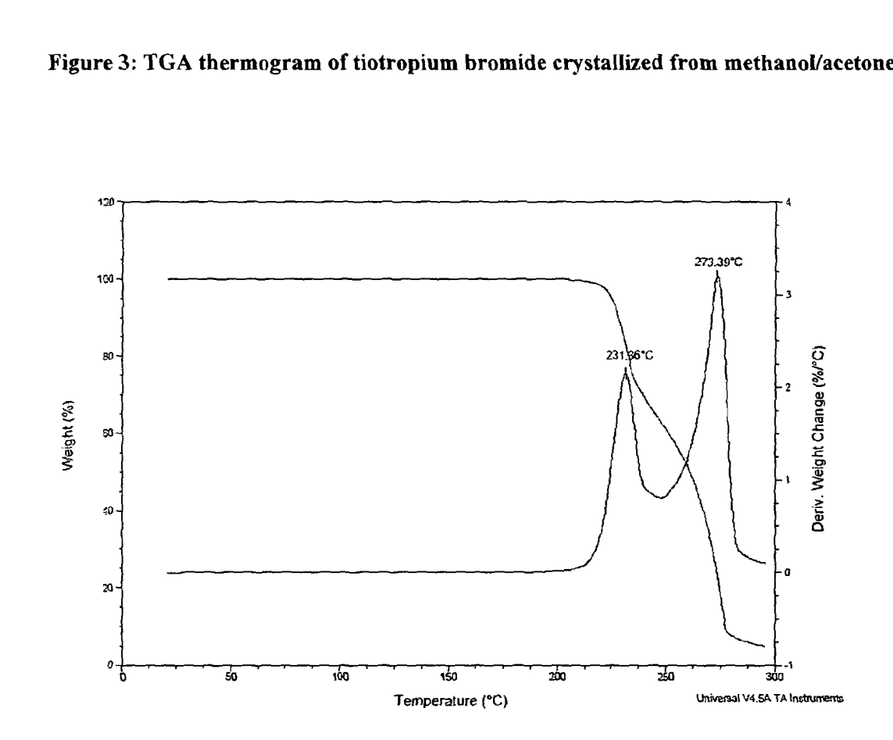
FIG. 3: TGA thermogram of tiotropium bromide crystallized from methanol/acetone.

Crude tiotropium bromide obtained according to the procedure presented above is crystallized from a mixture of methanol and acetone. Preferably, the material is dissolved in methanol at a temperature between about 45° C. and about 60° C., and acetone is added to the solution while maintaining the temperature of the solution between about 45° C. and about 60° C. Preferably, the resulting solution is cooled to a temperature between about −10° C. and about 0° C. and the resulting suspension is stirred at temperature between about −10° C. and about 0° C. over a period of about 2 hours. The desired product precipitates during cooling of the mixture. Preferably, tiotropium bromide is filtered, washed with acetone, and dried under reduced pressure, preferably under vacuum. The dried product has purity greater than 99.5% by HPLC and exhibits a single anhydrous crystalline form. The X-Ray Powder Diffraction (XRPD) diffractogram, the Differential Scanning Calorimetry (DSC) thermogram and the Thermogravimetric Analysis (TGA) thermogram are presented in FIGS. 1, 2 and 3, respectively.

In another preferred embodiment, the wet tiotropium bromide obtained from the methanol/acetone crystallization is dried under vacuum, firstly at temperature between about 45 and about 55° C. and secondly at temperature between about 100° C. and about 125° C. This temperature gradient avoids decomposition of tiotropium bromide during drying. When tiotropium bromide is directly dried at temperature between about 100° C. and about 125° C. decomposition into N-dexethyltiotropium occurs to small extension during drying; e.g. a wet product with a purity of 99.91% by HPLC and with no residual N-demethyltiotropium detected by HPLC (0.00% by HPLC) was dried overnight at 111° C. under reduced pressure. The material obtained after drying was 99.87% pure and the content of N-demethyltiotropium was 0.07% (by HPLC); another wet product with a purity of 99.59% and having a residual content of N-demethyltiotropium of 0.09% (by HPLC) was dried overnight at 111° C. under reduced pressure and the purity of the dried material decreased to 99.43% and the content of N-demethyltiotropium increased to 0.25%.

Figure 4:
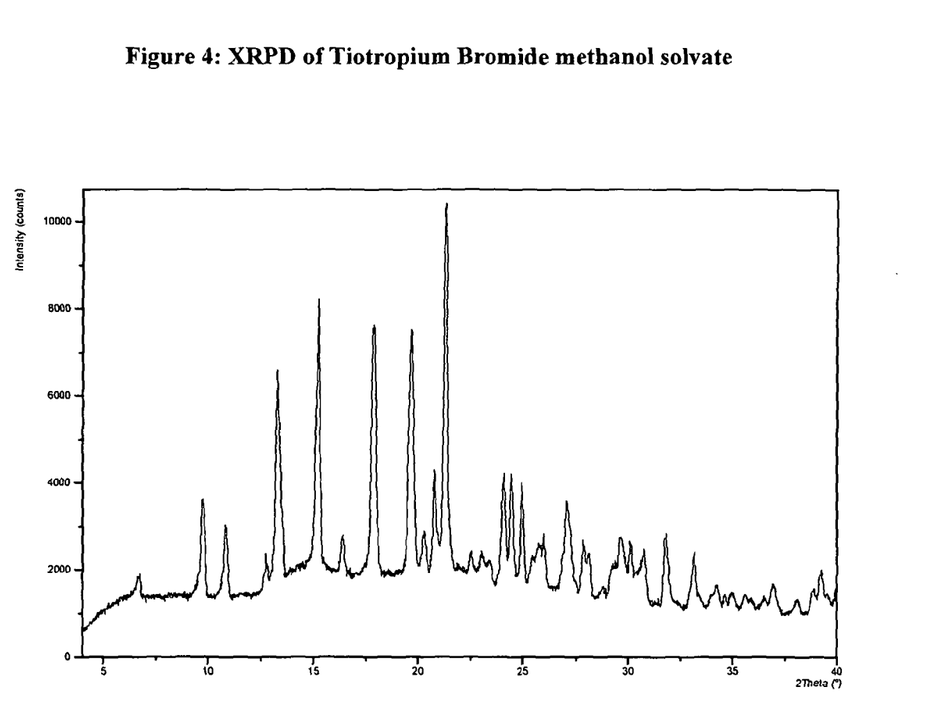
FIG. 4: XRPD of tiotropium bromide methanol solvate.
Figure 5:
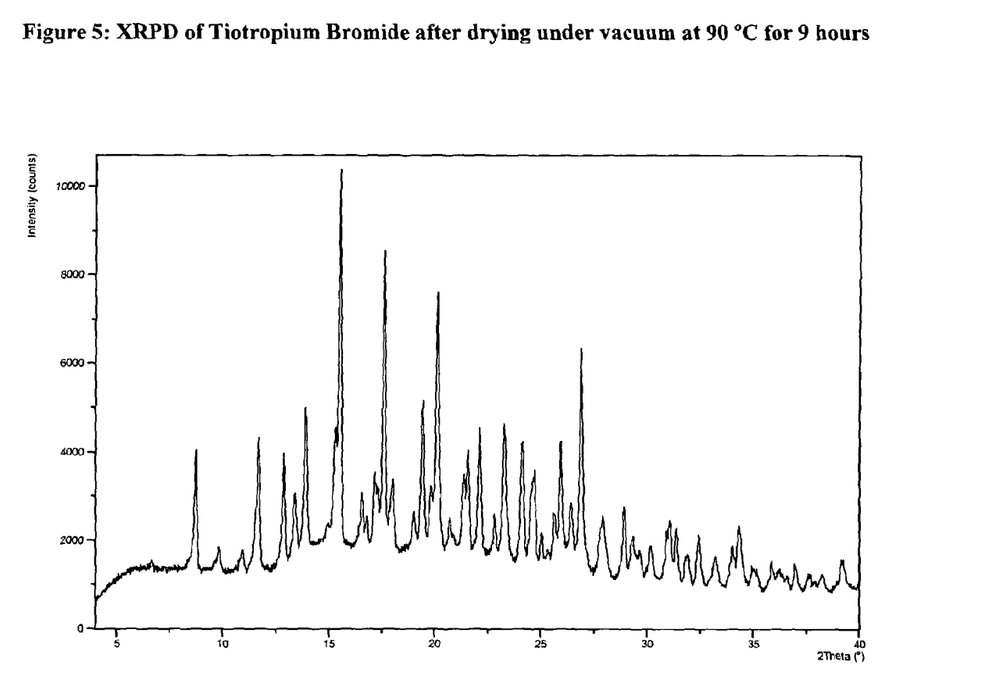
FIG. 5: XRPD of tiotropium bromide after drying under vacuum at 90° C. for 9 hours.
Figure 6:
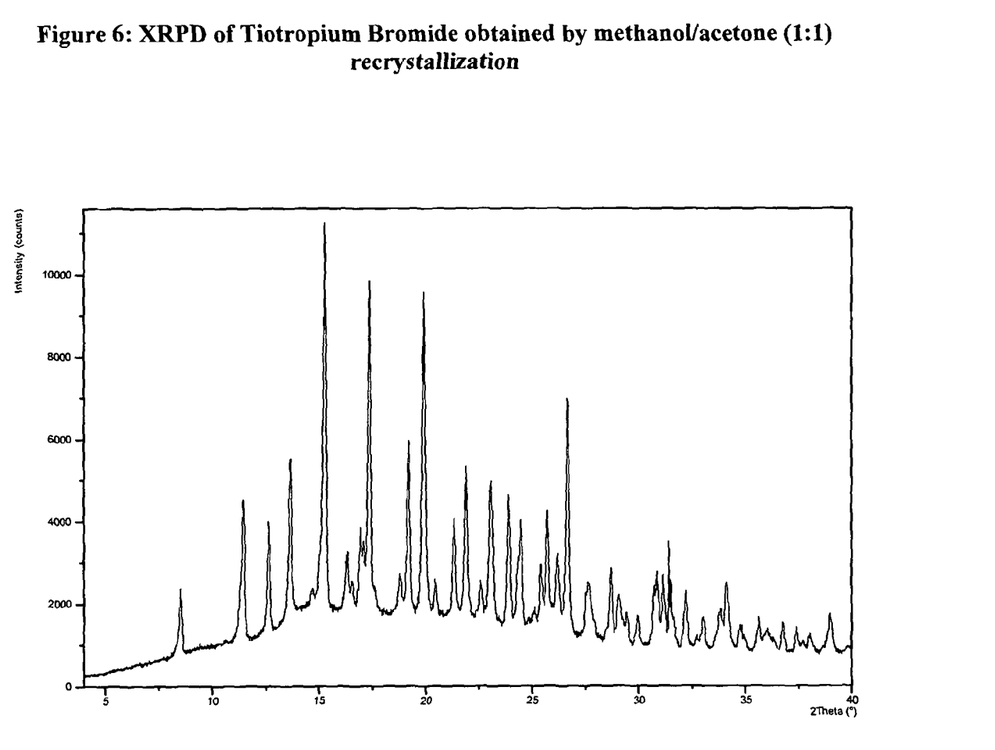
FIG. 6: XRPD of tiotropium bromide obtained by methanol/acetone (1:1) recrystallization.
Figure 7:
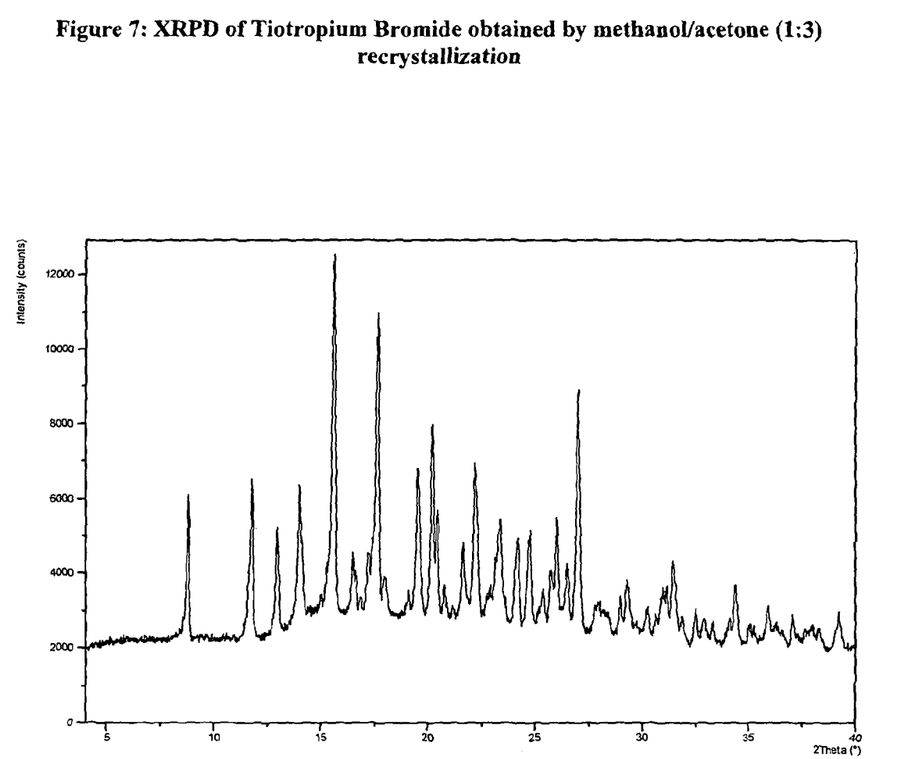
FIG. 7: XRPD of tiotropium bromide obtained by methanol/acetone (1:3) recrystallization.
Figure 8:
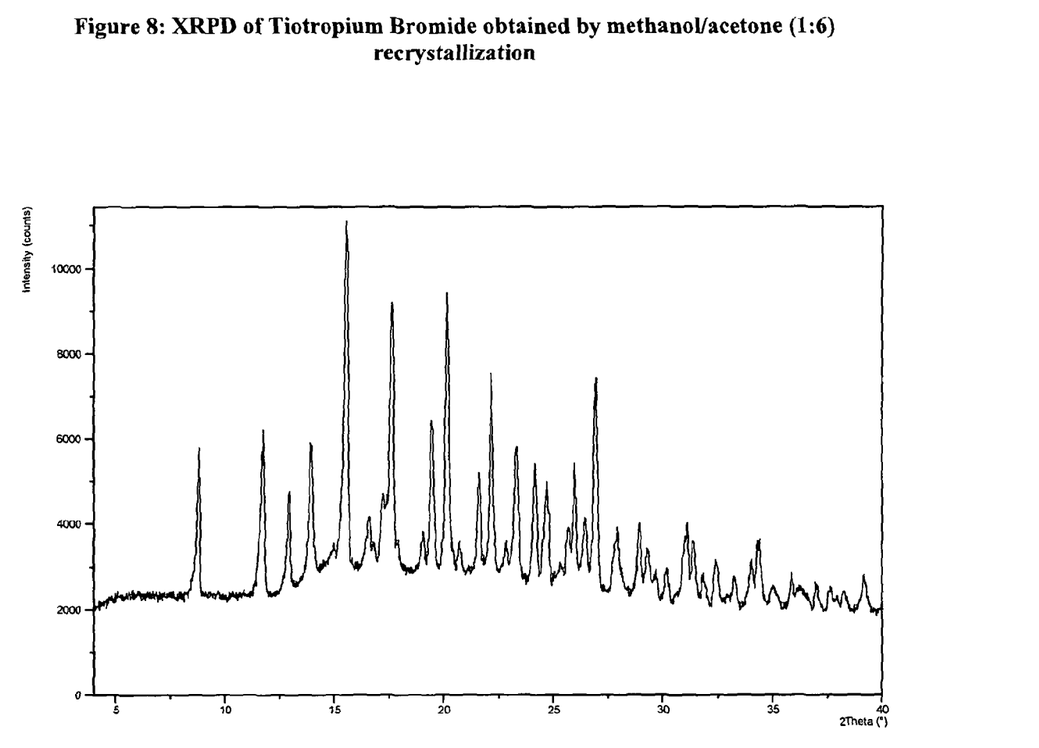
FIG. 8: XRPD of tiotropium bromide obtained by methanol/acetone (1:6) recrystallization.
Figure 9:
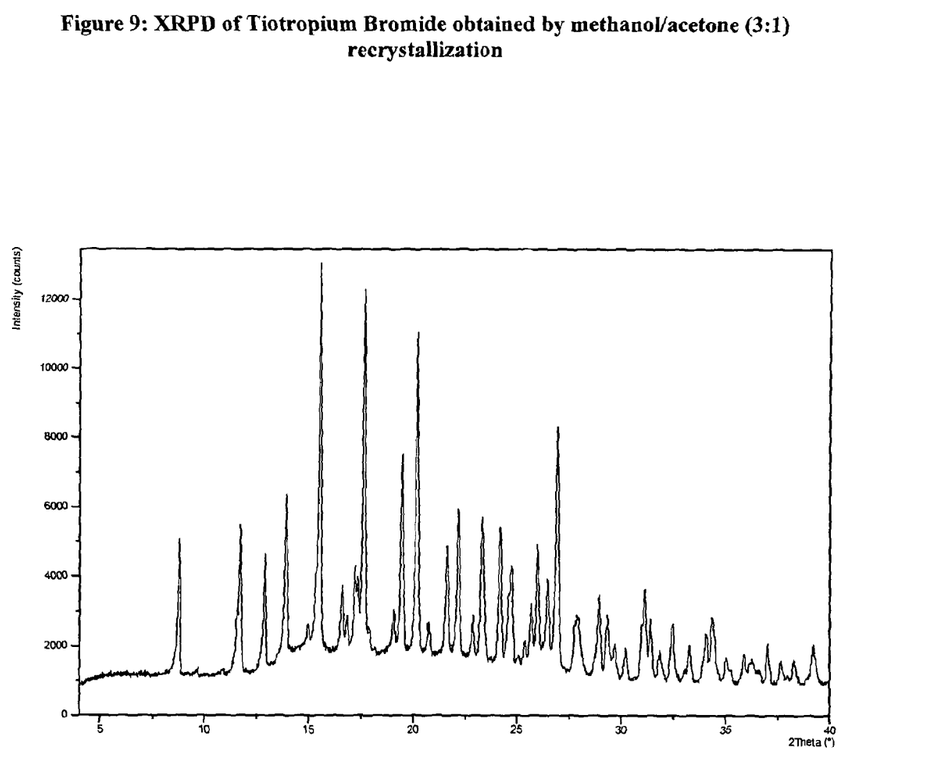
FIG. 9: XRPD of tiotropium bromide obtained by methanol/acetone (3:1) recrystallization.
Figure 10:
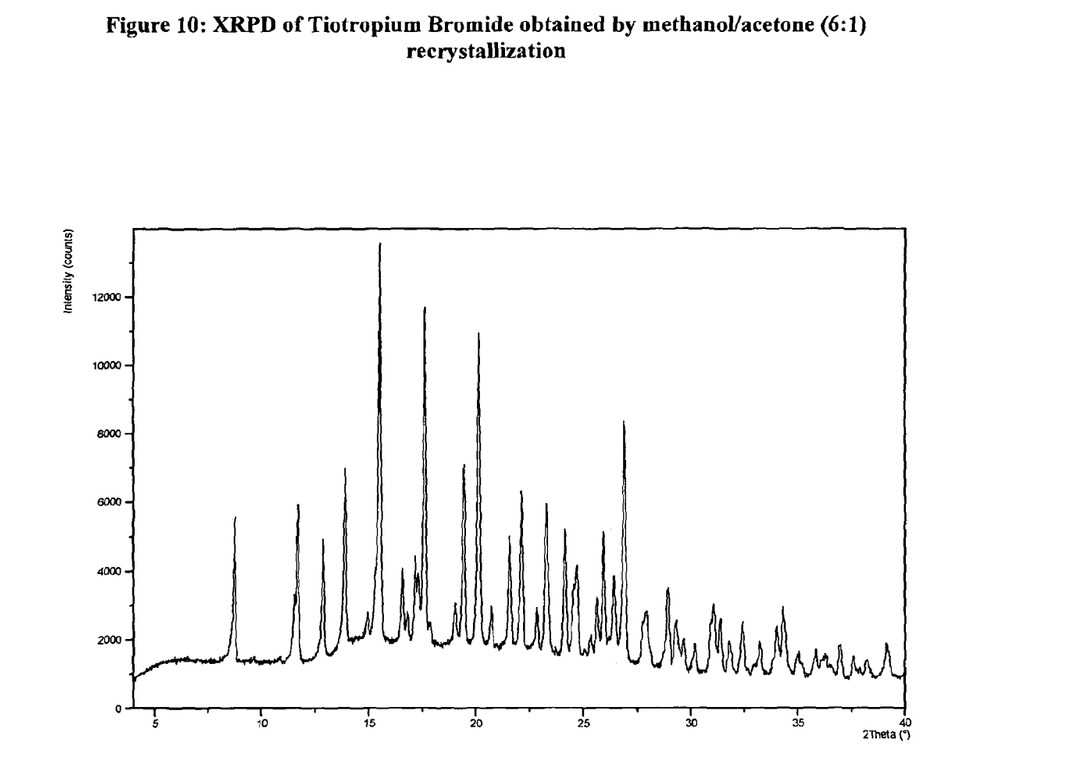
FIG. 10: XRPD of tiotropium bromide obtained by methanol/acetone (6:1) recrystallization.

Temperatures higher than about 90° C., under reduced pressure, are typically required to obtain the above-mentioned anhydrous crystalline form of tiotropium bromide. The wet material obtained from the crystallization step is a methanol solvate and, conversion of the methanol solvate into the anhydrous crystalline form takes place at temperatures higher than about 90° C., under reduced pressure. Wet tiotropium bromide in the form of methanol solvate (FIG. 4) was dried under vacuum at 90° C. over 9 hours; the XRPD diffractogram of the product exhibits a mixture of methanol solvate with anhydrous crystalline form (FIG. 5).

In another preferred embodiment, the crystallization of crude tiotropium bromide is carried out by dissolving the product in a mixture of ethanol and acetone at temperature between about 45° C. and about 60° C., cooling down the resulting solution to a temperature between about −10° C. and about 0° C., stirring the suspension at temperature between about −10° C. and about 0° C. for about 2 hours. Thereafter, the resulting product is isolated and dried at a first temperature of between about 45 and about 55° C. and followed by a second temperature of between about 100° C. and about 125° C. In still another. embodiment, the crystallization of crude tiotropium bromide is carried out by: (i) dissolving the product in methanol at ambient (room) temperature, (ii) concentrating the resulting solution under vacuum to a final volume (e.g. 6 vols.), (iii) adding acetone while maintaining the temperature between 35° C. and 60° C., (iv) cooling the resulting solution to a temperature of between about 0° C. and about −5° C., (v) stirring the suspension at temperature of between about 0° C. and about −5° C. for about 2 hours, and (vi) drying under vacuum, at a first temperature of between about 45 and about 55° C. and thereafter at a second temperature of between about 100° C. and about 125° C.

In another preferred embodiment, the same anhydrous crystalline form is obtained regardless of the proportion of methanol and acetone that are used in the crystallization of tiotropium bromide. For example, tiotropium bromide was crystallized according to the procedure described herein and from mixtures of methanol with the following proportions: methanol/acetone (1:1), methanol/acetone (1:3), methanol/acetone (1:6), methanol/acetone (3:1) and methanol/acetone (6:1). The XRPD diffractograms of the products (tiotropium bromide) obtained are presented in FIGS. 6-10.

Tiotropium bromide obtained from the methanol/acetone crystallization of the present invention is preferably micronized to obtain material with adequate particle size for inhalation. In another preferred embodiment, the present invention provides a micronization process for tailoring, the particle size whilst maintaining the polymorphic form of tiotropium bromide. The micronization process preferably comprises wet milling tiotropium bromide using a microfluidizer to induce cavitation at high pressure. Typically, the microfluidizer comprises at least one high pressure pump to force a suspension of tiotropium bromide in an anti-solvent through a nozzle or channel resulting in a pressure increase as the slurry, passes through the inlet and pressure decrease as the suspension exit the above mentioned channel/orifices. This pressure decrease results in a sufficient pressure decrease to cause vaporization and thus cavitation in the fluid stream which lead to cavitation stress and particle reduction. Preferably, the pressure is increased up to 2000 bar followed by a pressure drop. Particle to particle collisions and shear stress in the orifice/channels also promote the milling of the product; however the mechanism and contribution of all these mechanisms has not been clarified in the art. It is known to a skilled person in the art that the above effects can be controlled with the controlled of pressures, chamber/orifice design and number of passages. In a preferred embodiment, cavitation and/or particle to particle collision and/or shear stress is promoted by the passage of the suspension through small channels characterized by a geometry selected from the group consisting of: (i) a "Z" type single or multi slot geometry. and/or (ii) a "Y" type single or multi slot geometry. Examples of suitable anti-solvents for use in the micronisation process of the present invention include hydrocarbons such as heptane, or ethyl acetate, or acetone, or a mixture of two or more of such solvents.

After micronization under the conditions described above, the product is preferably isolated by feeding the suspension to a spray drier, wherein the drying temperature is preferably above about 90° C. Alternatively, the product can also be isolated by filtration of the suspension with the micronized material followed by drying the filtered product under vacuum, in an oven, at temperature of between about 100° C. and about 125° C.

The following examples are provided to illustrate the process claimed by this invention and are not intended to be construed as limitations of this invention; minor variations may be resorted to without departing from the spirit and scope of this invention.

Example 1

Preparation of N-demethyltiotropium

Scopine oxalate (47 g; 0.19 mol) was added to diethylamine (188 ml; 1.85 mol) followed by acetone (588 ml). The mixture was heated to a temperature between 40° C. and 45° C., was stirred at 40° C.-45° C. over 1 hour, was cooled to 20° C.-25° C. and filtered. Acetone (588 ml) was added to the filtered salts, the suspension was heated to 40° C.-45° C., was stirred at 40° C.-45° C. over 1 hour, was cooled to 20° C.-25° C. and filtered. The acetone filtered solution was combined with the filtered acetone/diethylamine solution. Acetone (588 ml) was added to the filtered salts, the mixture was heated to 40° C.-45° C., was stirred at 40° C.-45° C. over 1 hour, was cooled to 20° C.-25° C., was filtered and the salts were washed with acetone (188 ml). The solution and the wash were combined with the previously combined solutions. To the resulting solution dimethylformamide (30 ml) was added and the mixture was concentrated under vacuum at temperature below 45° C. until a final volume of 53 ml. MDTG (53.11 g; 0.21 mol) was added and the mixture stirred was for over 5 minutes. Then n-heptane (296 ml) was added followed by Zeolum 4A (23.5 g) and the mixture was stirred over 2 hours at room temperature. The zeolum was filtered and washed with n-heptane/DMF (30 ml; 3 ml). Anhydrous potassium carbonate (26.46 g; 0.19 mol) was added and the mixture was heated to a temperature between 90° C. and 95° C. under nitrogen atmosphere. The reaction mixture was stirred at 90° C.-95° C., under nitrogen atmosphere, until the reaction was considered complete. The content of MDTG in the reaction mixture was 3.74% by HPLC. The reaction mixture was cooled to 80° C., 2-methyltetrahydrofuran (876 ml) was added, the mixture was cooled to 20° C.-25° C., was filtered and the salts washed with 2-methyltetrahydrofuran (36 ml): The wash was combined with the main solution, and the combined solution was washed with brine (423 ml) until the content of DTG in the organic solution was 0.68%. The content of N-demethyltiotropium in the organic solution was 90.58% by HPLC. The organic solution was treated with activated charcoal, the activated charcoal was filtered, washed with 2-methytetrahydrofuran and the wash was combined with the main solution. The combined solution was concentrated under vacuum at temperature equal to, or lower than, 45° C. until a final volume of 71 ml. The suspension was cooled to −20° C.-(−15° C.), stirred at −20° C.-(−15° C.) over 12 hours, the product was filtered, washed with isopropanol (94 mil) previously cooled to 0° C.-5° C. and was dried. N-demethyltiotropium (20.24 g) was obtained with a purity of 99.36% by HPLC.

Example 2

Preparation of Crude Tiotropium Bromide

N-demethyltiotropium (66 g; 0.17 mol) was dissolved in dimethylformamide (330 ml) and the solution was cooled to a temperature between 0° C. and 5° C. A solution of bromomethane in 2-methyltetrahydrofuran (132 ml; 0.72 mol) was added and the reaction mixture stirred overnight at 0° C.-5° C. The content of N-demethyltiotropium in the reaction mixture was 3.6% by HPLC. Then the reaction mixture was heated up to a temperature between 10° C. and 15° C. and stirred at this temperature range over 2 hours. The content of N-demethyltiotropium in the reaction mixture decreased to 1.7%. The reaction mixture was heated to a temperature between 25° C. and 30° C. and stirred at that temperature range over 1 hour. The content of N-demethyltiotropium in the reaction mixture decreased to 1.0% by HPLC. 2-Methyltetrahydrofuran (594 ml) was added to the reaction mixture previously cooled to 0° C.-5° C., the suspension was stirred over 1 hour while maintaining the temperature between 0° C. and 5° C., the product was filtered and washed with 2-methyltetrahydrofuran (297 ml) previously cooled to a temperature between 0° C. and 5° C. The purity of the wet product was 99.48% and the content of N-demethyltiotropium was 0.33%/9 (by HPLC). The wet product was re-slurried in dimethylformamide (297 ml) over 1 hour, was filtered, was washed with 2-methyltetrahydrofuran (297 ml) previously cooled to 0° C.-5° C. and dried. Crude tiotropium bromide (80.4 g; 97.3% of the theoretical yield) was obtained with a purity of 99.77% and with a residual content of N-demethyltiotropium of 0.16% (by HPLC).

Example 3

Recrystallization of Crude Tiotropium Bromide

Crude tiotropium bromide (79 g) was dissolved in methanol (3555 ml) at reflux temperature. The solution was filtered and the filter was washed with methanol. The filtered solution was concentrated under vacuum to a final volume of 474 ml. Acetone (79 ml) was added while maintaining the mixture at temperature between 35° C. and 45° C. The mixture was cooled to a temperature between 0° C. and −5° C. and was stirred at 0° C.-(−5° C.) over 2 hours. The product was filtered and was washed with acetone (63 ml) previously cooled to a temperature between −5° C. and 0° C. The wet product was dried under vacuum at 50° C. overnight and after was dried under vacuum at 111° C. over 8 hours. Anhydrous crystalline tiotropium bromide (62.91 g) exhibiting an XRPD difractogram matching that presented in FIG. 1 and with a purity of 99.87% by HPLC was obtained. The content of N-demethyltiotropium in the product obtained was 0.03% by HPLC.

Example 4

Micronization of Tiotropium Bromide

Tiotropium bromide (9 g) was suspended in ethyl acetate (89.7 g) and stirred until a uniform suspension was obtained and afterwards the suspension was fed to a lab scale High Pressure Cavitation equipment operated at a pressure of 5 kPsi (345 bar) for 16 cycles. After the cavitation step the suspension was transferred to a holding vessel to be used in the next step. The suspension was fed to a lab scale spray dryer while stirring with a feed rate of 5 ml/min and drying temperature of 100° C.

Figure 11:
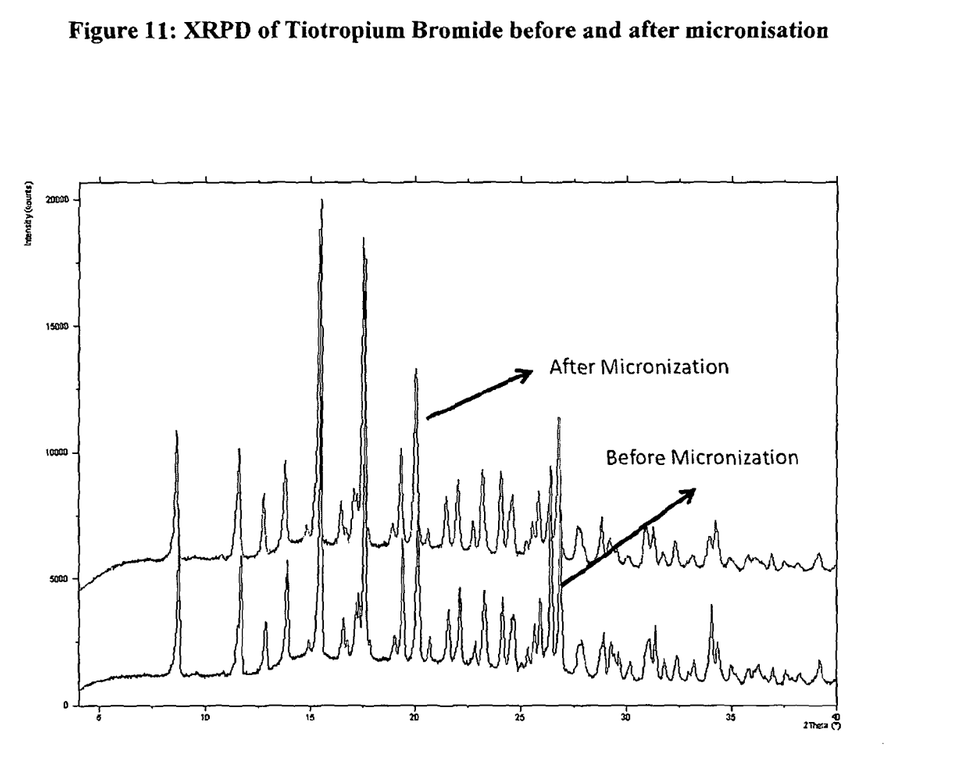
FIG. 11: XRPD of tiotropium bromide before and after micronization.

The product isolated presented an XRPD identical to the one of the starting material with a particle size distribution of Dv10=0.71 μm; Dv50=2.82 μm; Dv90=5.22 μm; span=1.6, as depicted in FIG. 11.

Micronized anhydrous crystalline tiotropium bromide obtained according to the invention was analyzed by X-ray powder diffraction. The X-ray powder patterns were recorded using the PANalytical X'Pert PRO X-ray diffraction system equipped with a copper source (Cu/Kα-1.54056 Å). The following table lists the characteristic peaks.

TABLE 1

X-ray powder reflections of micronized anhydrous crystalline tiotropium bromide.

| 2θ [°] | d [Å] |
|---|---|
| 8.66 | 10.22 |
| 11.59 | 7.64 |
| 12.77 | 6.93 |
| 13.80 | 6.42 |
| 14.83 | 5.98 |
| 15.41 | 5.75 |
| 16.46 | 5.38 |
| 16.68 | 5.32 |
| 17.09 | 5.19 |
| 17.20 | 5.15 |
| 17.52 | 5.06 |
| 18.93 | 4.69 |
| 19.33 | 4.59 |
| 20.03 | 4.43 |
| 20.60 | 4.31 |
| 21.48 | 4.14 |
| 22.04 | 4.03 |
| 22.74 | 3.91 |
| 23.19 | 3.84 |
| 24.05 | 3.70 |
| 24.59 | 3.62 |
| 25.25 | 3.53 |
| 25.54 | 3.49 |
| 25.85 | 3.45 |
| 26.34 | 3.38 |
| 26.80 | 3.33 |
| 27.80 | 3.21 |
| 28.82 | 3.10 |
| 29.21 | 3.06 |
| 30.07 | 2.97 |
| 30.94 | 2.89 |
| 31.28 | 2.86 |
| 31.71 | 2.82 |
| 32.32 | 2.77 |
| 33.12 | 2.71 |
| 33.93 | 2.64 |
| 34.23 | 2.62 |

The invention claimed is:
1. A process for preparing tiotropium bromide comprising:
   i) reacting scopine oxalate (X) with diethylamine in an inert solvent to form scopine (II)

ii) reacting scopine and methyl di-(2-dithienyl)glycolate (MDTG) in the presence of an inorganic base, and in an inert solvent to form N-demethyltiotropium;
   iii) reacting N-demethyltiotropium with bromomethane in an inert solvent to form tiotropium bromide (I)

iv) crystallizing tiotropium bromide in a mixture of methanol and acetone, and optionally thereafter,
   v) micronizing the tiotropium bromide so formed.
2. A process according to claim 1 further comprising:
   i) removing by filtration the diethylammonium salt formed by the reaction between scopine oxalate and diethylamine in step i); and
   ii) exchanging the reaction solvent.

3. A process according to claim 1 further comprising:
i) removing by filtration the inorganic salts formed during the transesterification reaction between scopine and MDTG in step ii); and
ii) washing the N-demethyltiotropium-containing solution with water or brine; and
iii) concentrating the resulting organic solution to crystallize the product, and thereafter filtering and drying the product to give N-demethyltiotrpium with a purity greater than 99.0% by HPLC.

4. A process according to claim 1 wherein:
i) tiotropium bromide formed by reaction between N-demethyltiotropium and bromomethane precipitates from the reaction mixture and thereafter more product is precipitated by addition of an anti-solvent; and optionally
ii) the tiotropium bromide so formed is re-slurried in a mixture of an inert solvent and anti-solvent; and
iii) tiotropium bromide is filtered and dried to isolate the product with a purity equal to, or greater than, 99.4% by HPLC.

5. A process according to claim 1 characterized in that the tiotropium bromide obtained from the crystallization of methanol and acetone has a purity greater than 99.5% by HPLC and is a single anhydrous crystalline form.

6. A process according to claim 1, wherein the inert solvent from step i) is selected from the group consisting of halogenated hydrocarbons, such as dichloromethane, and ketones, such as acetone.

7. A process according to claim 6, wherein the solvent is acetone.

8. A process according to claim 1, wherein the reaction of step i) is carried out at a temperature of between about 30° C. and about 45° C., preferably between about 40° C. and about 45° C.

9. A process according to claim 1, wherein the solvent of step ii) for the transesterification reaction is selected from the group consisting of mixtures of hydrocarbons, such as n-heptane, and amides, such as dimethylformamide.

10. A process according to claim 9, wherein the solvent is a mixture of n-heptane and dimethylformamide.

11. A process according to claim 10, wherein the solvent for the transesterification reaction is a mixture of 10 volumes of n-heptane with 1 volume of dimethylformamide.

12. A process according to claim 1, wherein the inorganic base in step ii) is anhydrous potassium carbonate, anhydrous cesium carbonate or potassium tert-butoxyde, preferably anhydrous potassium carbonate.

13. A process according to claim 1, wherein the transesterification reaction of step ii) is carried out at a temperature of between about 80° C. and about 110° C., preferably between about 85° C. and about 100° C., more preferably between about 90° C. and about 95° C.

14. A process according to claim 3, wherein the organic solution obtained after the water or brine washes in step ii) is treated with activated charcoal to remove color.

15. A process according to claim 1, wherein the solvent for the methylation reaction of step iii) is selected from the group consisting of amides, such as dimethylformamide, cyclic ethers, such as tetrahydrofuran or 2-methyltetrahydrofuran, nitriles, such as acetonitrile, and mixtures of acetone with tetrahydrofuran and of ethyl acetate with tetrahydrofuran.

16. A process according to claim 15, wherein the solvent is dimethylformamide.

17. A process according to claim 1, wherein the methylation reaction of step iii) is carried out at a temperature of between about 0° C. and about 5° C., followed by a temperature of between about 10° C. and about 15° C., followed by a temperature of between about 20° C. and 25° C.

18. A process according to claim 1, wherein the crystallization of tiotropium bromide in step iv) is carried out by dissolving the product in methanol and acetone at a temperature of between about 45° C. and about 60° C., followed by cooling to a temperature of between about 0° C. and about −5° C., followed by isolation by filtration and drying of the product.

19. A process according to claim 18, wherein the wet tiotropium bromide isolated from the methanol/acetone crystallization is dried under vacuum, at a first temperature of between about 45° C. and about 55° C., followed by drying at a second temperature of between about 100° C. and about 125° C.

20. A process according to claim 18, wherein the crystallization of tiotropium bromide is carried out by (i) dissolving the product in methanol at ambient (room) temperature; (ii) concentrating the methanol solution under vacuum, (iii) adding acetone whilst maintaining the temperature of the solution between about 35° C. and about 60° C., (iv) cooling the solution to a temperature of between about 0° C. and about −5° C., and (v) isolating the product by filtration and drying.

21. A process according to claim 1, wherein before the micronization of step v), tiotropium bromide is suspended in a solvent in which it is not soluble.

22. A process according to claim 21, wherein the solvent is a hydrocarbon, such as heptane, or ethyl acetate, or acetone, or a mixture of two or more such solvents.

23. A process according to claim 1, wherein the micronization in step v) is effected by cavitation and/or particle to particle collision and/or shear stress in the milling apparatus.

24. A process according to claim 23, wherein cavitation and/or particle to particle collision and/or shear stress is promoted by the passage of the suspension through small channels characterized by a geometry selected from the group consisting of: (i) a "Z" type single or multi slot geometry and/or (ii) a "Y" type single or multi slot geometry.

25. A process according to claim 23, wherein pressure is increased up to 2000 bar followed by a pressure drop.

26. A process according to claim 1, further comprising the step of isolating tiotropium bromide in the form of powder.

27. A process according to claim 26, wherein the isolation step comprises filtration and drying in an oven or spray drying.

28. A process according to claim 27, wherein the spray drying step is conducted with a drying temperature above about 90° C.

29. A process according to claim 1, wherein the crystalline form of tiotropium bromide obtained from the crystallization in step iv) is maintained during the micronization step v).

30. A process according to claim 29, wherein the crystalline form of tiotropium bromide is anhydrous.

31. A process according to claim 29, wherein the crystalline form obtained from the micronization step v) is maintained during the isolation step.

* * * * *